United States Patent
Ando et al.

(10) Patent No.: US 11,406,460 B2
(45) Date of Patent: Aug. 9, 2022

(54) SURGERY ASSISTING APPARATUS, METHOD OF CONTROLLING THE SAME, STORAGE MEDIUM, AND SURGERY ASSISTING SYSTEM

(71) Applicant: A-Traction Inc., Kashiwa (JP)

(72) Inventors: Takehiro Ando, Kashiwa (JP);
Hiroyuki Miyamoto, Kashiwa (JP);
Keita Awano, Kashiwa (JP); Yoshihide Sugiura, Kashiwa (JP)

(73) Assignee: A-TRACTION INC., Kashiwa (JP)

( * ) Notice: Subject to any disclaimer, the term of this patent is extended or adjusted under 35 U.S.C. 154(b) by 373 days.

(21) Appl. No.: 16/509,926

(22) Filed: Jul. 12, 2019

(65) Prior Publication Data

US 2019/0328469 A1 Oct. 31, 2019

Related U.S. Application Data

(63) Continuation of application No. PCT/JP2017/020699, filed on Jun. 2, 2017.

(30) Foreign Application Priority Data

Jan. 13, 2017 (JP) .............................. JP2017-004566

(51) Int. Cl.
*G05B 19/04* (2006.01)
*A61B 34/32* (2016.01)
(Continued)

(52) U.S. Cl.
CPC .............. *A61B 34/32* (2016.02); *B25J 13/088* (2013.01); *A61B 2034/2055* (2016.02);
(Continued)

(58) Field of Classification Search
CPC ........ B25J 13/08; B25J 13/088; B25J 9/1656; B25J 9/1689; A61B 2034/2055;
(Continued)

(56) References Cited

U.S. PATENT DOCUMENTS 7,841,980 B2 * 11/2010 Minosawa ........... A61B 1/0051
600/118
2008/0009697 A1 * 1/2008 Haider ................... A61B 90/11
600/407

(Continued)

FOREIGN PATENT DOCUMENTS

JP 2003-127076 A 5/2003
JP 2007-301378 A 11/2007
(Continued)

OTHER PUBLICATIONS

International Search Report dated Aug. 22, 2017, issued in counterpart International Application No. PCT/JP2017/020699, with English Translation (5 pages).

*Primary Examiner* — Harry Y Oh
(74) *Attorney, Agent, or Firm* — Oliff PLC

(57) ABSTRACT

A surgery assisting apparatus for controlling a posture of a first surgical tool to be inserted into a body cavity and mechanically driven, by using a second surgical tool to be inserted into the body cavity, comprises: a mode switch configured to switch a first mode and a second mode, the second surgical tool being used to control the first surgical tool in the second mode; one or more sensors configured to measure an angle and depth of insertion of a shaft of the second surgical tool into the body cavity; and at least one memory and at least one processor which function as a computing unit configured to determine a target position of a control point that is a point for specifying the posture of the first surgical tool in order to control the posture of the first surgical tool.

19 Claims, 7 Drawing Sheets

(51) Int. Cl.
  *B25J 13/08* (2006.01)
  *A61B 34/20* (2016.01)
  *A61B 34/30* (2016.01)
  *A61B 90/00* (2016.01)
(52) U.S. Cl.
  CPC ... *A61B 2034/302* (2016.02); *A61B 2090/062* (2016.02); *A61B 2090/067* (2016.02)
(58) Field of Classification Search
  CPC ........ A61B 2034/302; A61B 2090/062; A61B 2090/067; A61B 34/30; A61B 34/32; A61B 2034/2068; A61B 34/20; A61B 34/70
  See application file for complete search history.

(56) References Cited

U.S. PATENT DOCUMENTS

| | | | | |
|---|---|---|---|---|
| 2008/0125794 | A1* | 5/2008 | Brock | A61B 34/30 606/130 |
| 2009/0076555 | A1* | 3/2009 | Lowry | A61B 17/70 606/280 |
| 2013/0023730 | A1* | 1/2013 | Kitamura | A61B 1/3132 600/104 |
| 2016/0213436 | A1* | 7/2016 | Inoue | A61B 17/3421 |
| 2016/0374541 | A1* | 12/2016 | Agrawal | A61B 1/0052 600/102 |
| 2018/0014851 | A1* | 1/2018 | Hansen | A61B 17/3403 |
| 2018/0023946 | A1* | 1/2018 | Elliot | G01B 11/002 356/614 |
| 2018/0049794 | A1* | 2/2018 | Swayze | B25J 13/089 |
| 2018/0049795 | A1* | 2/2018 | Swayze | A61B 17/320092 |
| 2018/0078315 | A1* | 3/2018 | Ren | A61B 3/1025 |

FOREIGN PATENT DOCUMENTS

| | | | | |
|---|---|---|---|---|
| JP | 2009082625 A | * | 4/2009 | |
| WO | WO-2011150257 A2 | * | 12/2011 | ............. G09B 23/28 |
| WO | 2015-119012 A1 | | 8/2015 | |
| WO | WO-2015129368 A1 | * | 9/2015 | ......... A61B 1/00098 |

* cited by examiner

SURGERY ASSISTING APPARATUS, METHOD OF CONTROLLING THE SAME, STORAGE MEDIUM, AND SURGERY ASSISTING SYSTEM

CROSS-REFERENCE TO RELATED APPLICATIONS

This application is a continuation of International Patent Application No. PCT/JP2017/020699 filed on Jun. 2, 2017, which claims priority to and the benefit of Japanese Patent Application No. 2017-004566 filed on Jan. 13, 2017, the entire disclosures of which are incorporated herein by reference.

BACKGROUND OF THE INVENTION

Field of the Invention

The present invention relates to a surgery assisting apparatus, a method of controlling the same, a storage medium, and a surgery assisting system.

Description of the Related Art

A laparoscopic surgery by which a plurality of small-diameter holes are formed in the abdominal wall and an operator performs a surgery by inserting medical tools such as a surgical tool and an endoscope held in his or her hands into the body cavity through these holes is known. This laparoscopic surgery is generally performed such that a scopist who manipulates a laparoscope and an assistant who, for example, pulls an organ by a forceps assist an operator who performs a surgery by manipulating a plurality of surgical tools such as an ultrasonic scalpel and a forceps. This sometimes complicates the laparoscopic surgery compared to an abdominal surgery performed by incising the abdomen. Accordingly, a technique of assisting an operator by a robot arm instead of assistance by the scopist and the like has been proposed.

Japanese Patent Laid-Open No. 2003-127076 has proposed a technique that measures the posture of a surgical tool by using a movable coil attached to a medical treatment tool and a fixed transmitter attached to a vertical multijoint 6-degree-of-freedom robot including a scope, and controls the posture of a laparoscope so that the distal end position of the surgical tool passes over the axis of the laparoscope. Also, Japanese Patent Laid-Open No. 2007-301378 has proposed a technique that measures the posture of a surgical tool by installing an inertia sensor such as an inclination sensor and an insertion amount sensor in a trocar, and controls the posture of a laparoscope by following the distal end position of the surgical tool.

Unfortunately, the technique proposed in Japanese Patent Laid-Open No. 2003-127076 is expensive because the 6-degree-of-freedom posture must be obtained, and a measurement error for each degree of freedom sometimes largely affects the control of the robot arm. Also, when measuring the movement of a surgical tool to be manipulated by using the inertia sensor as disclosed in the technique proposed by Japanese Patent Laid-Open No. 2007-301378, measurement errors called drift errors are actually accumulated, and the measurement results deviate from the actual positions. That is, if the measurement errors are accumulated in the measurement results for the surgical tool, the action of the robot arm becomes unnatural.

In addition, in either technique, an intentional manipulation target of an operator is a main surgical tool for a medical treatment, and a secondary surgical tool such as a laparoscope is controlled in accordance with the movement of the distal end position of the main surgical tool. That is, neither technique takes account of a case in which an intentional manipulation target of an operator is a secondary surgical tool, and the operator intuitively manipulates the posture of the secondary surgical tool by using a main surgical tool. If the purpose of the main surgical tool switches from the purpose of a medical treatment to the purpose of directly manipulating the secondary surgical tool and the operator can desirably manipulate the secondary surgical tool, it is possible to further enhance the effect of assisting the operator by the robot arm.

SUMMARY OF THE INVENTION

The present invention has been made in consideration of the above-described problem. The present disclosure has been made in consideration of the aforementioned issues, and realizes technique capable of intuitively controlling the posture of a mechanically controlled surgical tool by using a surgical tool for a medical treatment while suppressing the influence of measurement errors.

In order to solve the aforementioned problems, one aspect of the present disclosure provides a surgery assisting apparatus for controlling a posture of a first surgical tool to be inserted into a body cavity and mechanically driven, by using a second surgical tool to be inserted into the body cavity, comprising: a mode switch configured to switch a first mode in which the second surgical tool is used to perform a medical treatment, and a second mode in which the second surgical tool is used to control the first surgical tool; one or more sensors configured to measure an angle and depth of insertion of a shaft of the second surgical tool into the body cavity; and at least one memory and at least one processor which function as a computing unit configured to determine, based on a result of measurement by the one or more sensors, a target position of a control point that is a point for specifying the posture of the first surgical tool and is a control target of an operator, in order to control the posture of the first surgical tool, wherein the computing unit determines the target position of the control point in accordance with change amounts of the measured insertion angle and insertion depth from a start timing of the second mode.

Another aspect of the present disclosure provides, a surgery assisting apparatus for controlling a posture of a first surgical tool to be inserted into a body cavity and mechanically driven, by using a second surgical tool to be inserted into the body cavity, comprising: one or more sensors configured to measure an angle and depth of insertion of a shaft of the second surgical tool into the body cavity; and at least one memory and at least one processor which function as: an obtaining unit configured to obtain a position of a control point that is a point for specifying the posture of the first surgical tool and is a control target of an operator; and a computing unit configured to determine a target position of the control point based on a result of measurement by the one or more sensors, in order to control the posture of the first surgical tool, wherein the computing unit determines the target position of the control point in accordance with change amounts of the measured insertion angle and insertion depth from a reference time at which control of the first surgical tool is started by using the second surgical tool.

Still another aspect of the present disclosure provides, a method of controlling a surgery assisting apparatus for controlling a posture of a first surgical tool to be inserted into a body cavity and mechanically driven, by using a second surgical tool to be inserted into the body cavity, comprising: switching a first mode in which the second surgical tool is used to perform a medical treatment, and a second mode in which the second surgical tool is used to control the first surgical tool; measuring an angle and depth of insertion of a shaft of the second surgical tool into the body cavity; and determining, based on a result of the measurement, a target position of a control point that is a point for specifying the posture of the first surgical tool and is a control target of an operator, in order to control the posture of the first surgical tool, wherein the target position of the control point is determined in accordance with change amounts of the measured insertion angle and insertion depth from a start timing of the second mode.

Yet another aspect of the present disclosure provides, a non-transitory computer-readable storage medium storing a program for causing a computer to execute a method of controlling a surgery assisting apparatus for controlling a posture of a first surgical tool to be inserted into a body cavity and mechanically driven, by using a second surgical tool to be inserted into the body cavity, the method comprising: switching a first mode in which the second surgical tool is used to perform a medical treatment, and a second mode in which the second surgical tool is used to control the first surgical tool; measuring an angle and depth of insertion of a shaft of the second surgical tool into the body cavity; and determining, based on a result of the measurement, a target position of a control point that is a point for specifying the posture of the first surgical tool and is a control target of an operator, in order to control the posture of the first surgical tool, wherein the target position of the control point is determined in accordance with change amounts of the measured insertion angle and insertion depth from a start timing of the second mode.

Still yet another aspect of the present disclosure provides, a surgery assisting system including a surgery assisting apparatus and a medical instrument driving apparatus, wherein the surgery assisting apparatus is a surgery assisting apparatus for controlling a posture of a first surgical tool to be inserted into a body cavity and mechanically driven, by using a second surgical tool to be inserted into the body cavity, and comprises: a mode switch configured to switch a first mode in which the second surgical tool is used to perform a medical treatment, and a second mode in which the second surgical tool is used to control the first surgical tool; one ore more sensors configured to measure an angle and depth of insertion of a shaft of the second surgical tool into the body cavity; and at least one memory and at least one processor which function as computing unit configured to determine, based on a result of measurement by the one or more sensors, a target position of a control point that is a point for specifying the posture of the first surgical tool and is a control target of an operator, in order to control the posture of the first surgical tool, wherein the computing unit determines the target position of the control point in accordance with change amounts of the measured insertion angle and insertion depth from a start timing of the second mode, and wherein the medical instrument driving apparatus comprises driving unit configured to control the posture of the first surgical tool, such that the position of the control point of the first surgical tool is the same as the target position of the control point determined by the computing unit of the surgery assisting apparatus.

According to the present invention, it is possible to intuitively control the posture of a mechanically controlled surgical tool by using a surgical tool for a medical treatment while suppressing the influence of measurement errors.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF EMBODIMENTS

Exemplary embodiments of the present invention will be explained in detail below with reference to the accompanying drawings. Note that in the following explanation, a case in which the posture of a surgical tool is simply measured or controlled sometimes includes a case in which the position of a specific portion of the surgical tool is measured or the specific portion of the surgical tool is controlled to another position.

(Configuration of Surgery Assisting System)

Figure 1:
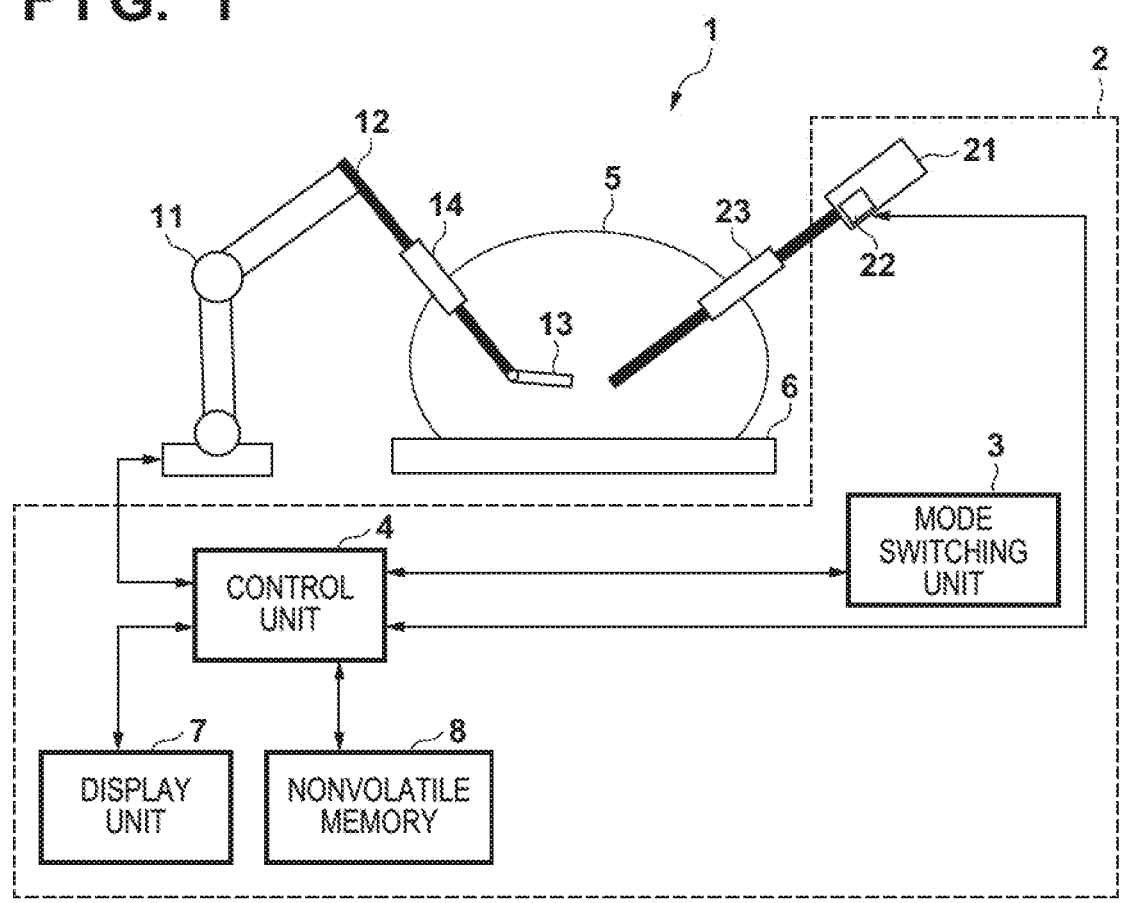
FIG. 1 is a view showing a configuration example of a surgery assisting system according to an embodiment.

FIG. 1 is a view showing a functional configuration example of a surgery assisting system 1 according to an embodiment. Note that one or more functional blocks shown in FIG. 1 can be implemented by hardware such as an ASIC or a PLA (Programmable Logic Array), and can also be implemented by a programmable processor such as a CPU or an MPU by executing software. It is also possible to implement one or more functional blocks by combining software and hardware. In the following explanation, therefore, even when different functional blocks are described as main operation units, they can be implemented by the same hardware as a main unit.

The surgery assisting system 1 according to this embodiment includes a surgery assisting apparatus 2, and a medical instrument driving unit 11 for controlling the posture of a surgical tool or an end effector. The surgery assisting apparatus 2 includes a position/posture measurement device 22 for measuring the posture of a surgical tool held by an operator, a mode switching unit 3 for switching control states, a control unit 4 for controlling calculations of coordinate conversion, the position of a control target, and the like, and controlling the medical instrument driving unit 11, a display unit 7, and a nonvolatile memory 8. FIG. 1 shows the way a surgical tool and an end effector are inserted through sheath tubes into the body cavity of a patient lying on an operating table 6.

The surgery assisting system 1 according to this embodiment is installed near an operator and a patient, and assists an operation performed by the operator by controlling the medical instrument driving unit 11 in cooperation with manipulation of a surgical tool by the operator. The operator can alternately switch a medical treatment (for example, incision of a part of an organ by an electric scalpel), and control of the posture of a robot medical instrument 12 or an end effector (conventionally, an assistant pulls an organ by using a forceps), by manipulating a handheld medical instrument 21.

Accordingly, unlike the above-described control that always measures the distal end position of a surgical tool and causes a laparoscope or the like to follow the distal end position and its vicinity, the control of the posture of the robot medical instrument 12 or the end effector according to this embodiment is performed in the interval of manipulation of the handheld medical instrument 21 for a medical treatment such as incision. Therefore, the measurement of the posture of the handheld medical instrument 21, which is performed to control the posture of the robot medical instrument 12 or the end effector, is completed within a relatively short time.

The medical instrument driving unit 11 includes a driving unit (for example, a robot arm) for controlling the movement of the robot medical instrument 12 and the posture of an end effector 13. For example, the driving unit can control the insertion angle of the robot medical instrument 12 to an abdominal wall 5, the movement (insertion depth) of the robot medical instrument 12 in the long-axis direction of a shaft, and the driving of the end effector 13. The mechanism of the driving unit can be, for example, a mechanism using an R guide, a mechanism using a parallel link, or a mechanism using a vertical multijoint arm, and the mechanism can have an arbitrary shape as long as the mechanism can actively control the posture of the end effector 13. The driving unit includes a plurality of positioning actuators such as servo motors, and current position information such as a joint angle of the mechanism can be obtained from an encoder included in each actuator. The medical instrument driving unit 11 is connected to the surgery assisting apparatus 2 via a communication path such as a LAN or a bus, and exchanges data with the control unit 4 of the surgery assisting apparatus 2. The medical instrument driving unit 11 can output current position information such as a joint angle to the control unit 4 of the surgery assisting apparatus 2, and can control the movement of the robot medical instrument 12 and the posture of the end effector 13 based on control information output from the control unit 4. Note that in the following explanation, a simple term "robot" indicates all of the medical instrument driving unit 11, the robot medical instrument 12, and the end effector 13.

A part of the robot medical instrument 12 is inserted into the body cavity through a sheath tube 14 inserted into a small-diameter hole formed in the abdominal wall 5. For example, the robot medical instrument 12 includes a forceps, a pair of tweezers, an electric scalpel, an aspiration tube, an ultrasonically activated scalpel, a hemostatic device, a radiofrequency ablation device, an endoscope, a thoracoscope, and a laparoscope. The robot medical instrument 12 can have a straight shape, and can also have a bending joint.

The handheld medical instrument 21 is a medical instrument which an operator actually moves with a hand to perform a medical treatment, and is inserted into the body cavity through a sheath tube 23 inserted into a small-diameter hole formed in the abdominal wall 5. The position/posture measurement device 22 is attached to the handheld medical instrument 21, and measures the posture of the handheld medical instrument 21 by a sensor (to be described later). This sensor can be a general sensor capable of measuring a 6-degree-of-freedom absolute position/posture. In this embodiment, however, an example using a sensor capable of measuring only a relative position/posture from a given time and a given position will be explained.

The position/posture measurement device 22 is configured by a combination of an inertia sensor capable of measuring a 3-degree-of-freedom posture, and a distance sensor capable of measuring the depth of insertion into the body cavity. As the inertia sensor, it is possible to use, for example, a general sensor such as an acceleration sensor, an inclination sensor, a gyro sensor, or a magnetic field sensor, or a combination of these sensors. Also, as the distance sensor, it is possible to use, for example, an encoder using a roller that rotates when the handheld medical instrument 21 is inserted, or a range finder using light or magnetism.

The mode switching unit 3 includes a manipulation member for appropriately switching manipulation modes of the surgery assisting system. This manipulation member is a hand switch, a foot switch, or the like. The manipulation modes include a mode (to be also simply called a treatment mode) in which an operator actually performs a surgery by manipulating the handheld medical instrument 21 in order to perform a medical treatment, and a mode (to be also simply called a robot manipulation mode) in which the handheld medical instrument 21 is used to manipulate the robot medical instrument 12 or the end effector. The robot manipulation mode further includes a calibration mode for performing calibration (to be described later), and a position control mode for controlling the position of a predetermined portion of the robot medical instrument 12 or the like by using the handheld medical instrument 21. When the operator switches the manipulation modes by using the mode switching unit 3, the control unit 4 switches the manipulation modes of the system in accordance with a signal from the mode switching unit 3, and records the current manipulation mode in a RAM (not shown). Note that it is also possible to obtain information such as a predetermined voice or a predetermined gesture via the mode switching unit 3, and cause the control unit 4 to perform switching to a manipulation mode corresponding to the input information.

The control unit 4 includes a central arithmetic unit such as a CPU or an MPU, a ROM, and a RAM, and controls the operation of each block of the surgery assisting apparatus 2 by executing a program stored in a storage device such as the ROM or the nonvolatile memory 8. Also, the control unit 4 obtains current position information such as joint angles (or distance information between the joint angles or the like obtained based on the current position information) from the medical instrument driving unit 11. In addition, the control unit 4 transmits control information for controlling the movement of the robot medical instrument 12 and the posture of the end effector 13 to the medical instrument driving unit 11.

The display unit 7 includes a display device such as a liquid crystal display or an organic EL display, and displays a still image or a moving image of the body cavity captured by a laparoscope (not shown) inserted into the abdominal wall. The display unit 7 also displays, for example, the internal state (including, for example, numerical values indicating the postures of the robot and the handheld medical instrument 21) of the system, and a manipulation screen for manipulating this system.

The nonvolatile memory 8 includes a recording medium such as a semiconductor memory or a magnetic disk, and stores programs to be executed by the control unit 4, constants for operations, and the like.

(Problems when Measuring Posture of Handheld Medical Instrument 21)

To manipulate the robot medical instrument 12 by using the handheld medical instrument 21, the posture of the handheld medical instrument 21 must be measured. To obtain the posture, this embodiment uses a coordinate system using the rotation center in the abdominal wall 5 as an origin and based on the posture when the inertia sensor is activated. However, a posture measurement method like this has the following three problems.

First, the coordinate system of the inertia sensor and the coordinate system of the robot are different. Even when the posture of the handheld medical instrument 21 is measured, therefore, the robot medical instrument 12 or the end effector 13 cannot be moved in a direction intended by the operator.

Second, the inertia sensor contains a drift error in a measurement value of a rotational angle around the gravity axis. The inertia sensor generally calculates the posture by combining a gyro sensor and an acceleration sensor. However, only the value of the gyro sensor can be used for the rotational angle around the gravity axis. Accordingly, a value obtained by integrating the angular velocity is used as the rotational angle. Since the measurement result of the angular velocity more or less contains an error, this measurement error increases with time if the value of the angular velocity is integrated. This measurement error is called a drift error. If the drift error occurs, the initially defined coordinate system looks as if it were rotated, and the actual posture of the handheld medical instrument and the measurement value deviate from each other. Note that even when using only the acceleration sensor without using any gyro sensor, the measurement result similarly contains a drift error because a value obtained by integrating the acceleration is used as the position.

Third, it is difficult to match the reference point of the distance sensor for measuring the insertion depth with the rotation center of the abdominal wall. The distance sensor included in the position/posture measurement device 22 is normally installed in a predetermined position on the sheath tube 23 or the handheld medical instrument 21, so only the distance based on this position can be measured. Therefore, the reference point of the distance sensor is different from the rotation center of the handheld medical instrument 21 in the abdominal wall 5. However, the rotation center in the abdominal wall 5 exists inside the abdominal wall and changes due to, for example, the thickness of the abdominal wall, and hence cannot be determined at a predetermined distance from the sheath tube 23. That is, if it is impossible to mutually convert the rotation center of the handheld medical instrument 21 and the reference point of the distance sensor, the origin of the handheld medical instrument 21 cannot accurately be obtained on the robot coordinate system, and unnatural manipulation occurs.

(Series of Operations According to Manipulation of Robot Medical Instrument Using Handheld Medical Instrument 21)

Figure 9:
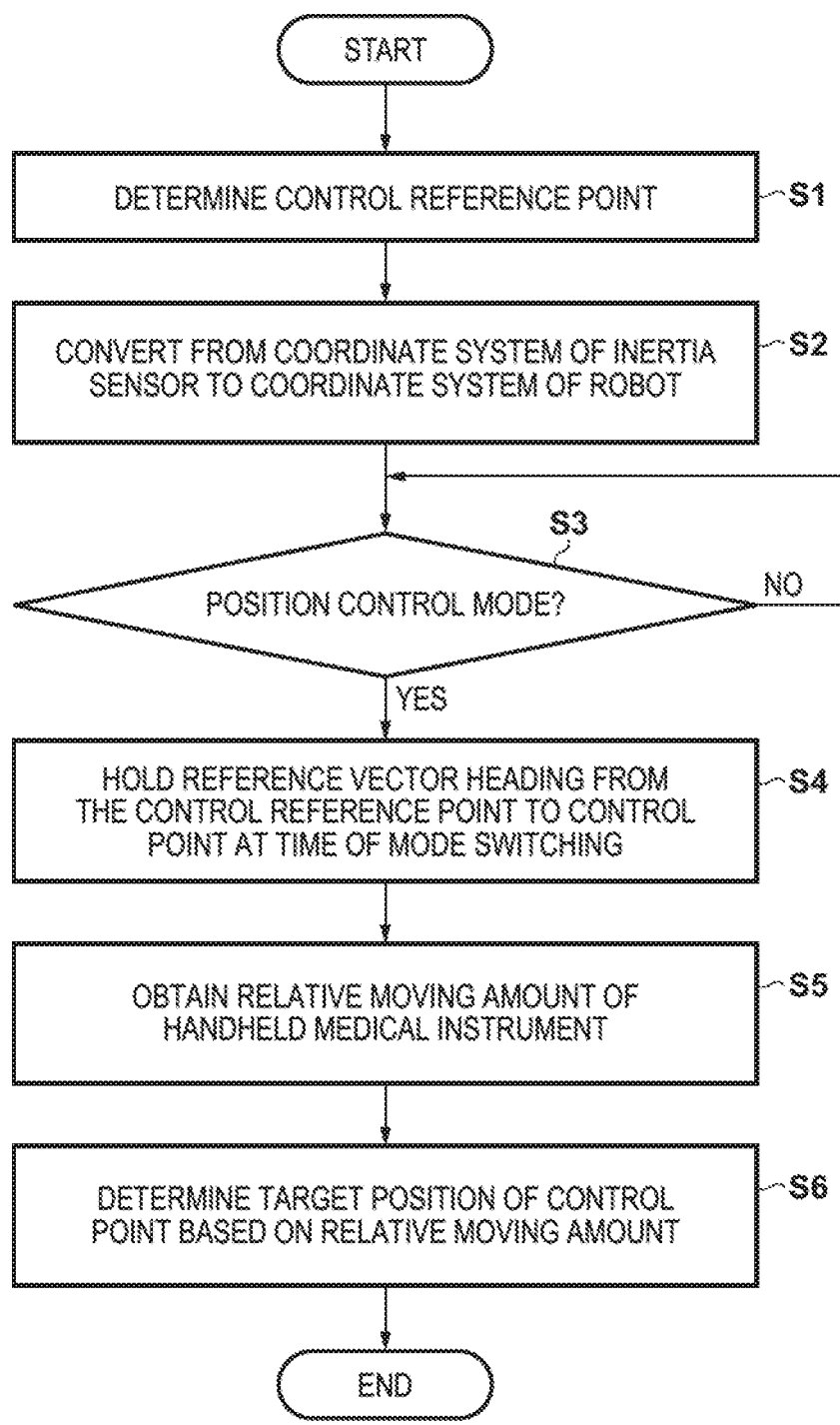
FIG. 9 is a flowchart showing a series of operations for manipulating a robot medical instrument by using a hand-held medical instrument according to the embodiment.

A series of operations according to the manipulation of the robot medical instrument 12 using the handheld medical instrument 21 will be explained below with reference to FIG. 9. Although individual steps will be explained in detail later, these operations can eliminate the above-described problems, and enable the operator to intuitively manipulate the robot medical instrument 12 or the end effector 13 by using the handheld medical instrument 21. Note that the control unit 4 implements the operations by deploying programs stored in the nonvolatile memory 8 onto the RAM and executing the programs. Note also that this processing is started when the operator switches the manipulation mode to the calibration mode by manipulating the mode switching unit 3.

In step S1, the control unit 4 determines a control reference point to be used as a virtual rotation center. In this embodiment, the control reference point is set in the same position as the rotation center of the handheld medical instrument 21. Therefore, the control unit 4 determines the position of the rotation center of the handheld medical instrument 21 (that is, the position of the control reference point) in the coordinate system of the inertia sensor based on the measurement result obtained by calibration (to be described in detail later).

In step S2, the control unit 4 converts the coordinate system of the inertia sensor into the coordinate system of the robot. More specifically, from the relationship between the position in the coordinate system of the inertia sensor and the position in the coordinate system of the robot with respect to at least two positions specified by calibration in step S1, the control unit 4 determines a conversion function between the coordinate systems.

In step S3, the control unit 4 determines whether an instruction for switching to the position control mode is received. For example, if the operator sets the manipulation mode to the position control mode via the mode switching unit 3 after the processing in step S2 is complete, the control unit 4 receives an instruction for switching the manipulation mode to the position control mode. If the manipulation mode switching instruction is received, the control unit 4 advances the process to step S4. On the other hand, if no manipulation mode switching instruction is received, the control unit 4 returns the process to step S3 (the control unit 4 may also terminate the series of operations if necessary).

In step S4, the control unit 4 calculates a reference vector heading from the control reference point to a control point at the time at which the manipulation mode is switched to the position control mode. The "control point" is a point as a control target when the operator manipulates the robot medical instrument 12 or the end effector 13. The control unit stores information of the calculated reference vector in the RAM or the like. In this process, a virtual shaft defined at the mode switching timing and extending from the control reference point to the control point is determined and held.

In step S5, the control unit 4 obtains a relative moving amount of the handheld medical instrument 21 from the time at which the reference vector is calculated (that is, the time at which the manipulation mode is switched to the position control mode). In step S6, the control unit 4 moves the reference vector based on the relative moving amount obtained in step S5, thereby determining a target position indicating a position where the control point is supposed to exist. In other words, the target position of the distal end of the virtual shaft obtained in step S4 is determined in accordance with the relative moving amount by which the operator has moved the handheld medical instrument 21. After that, the control unit 4 moves the end effector 13 to the target position by controlling the robot arm, and terminates the series of operations.

In this processing as described above, the influence of a drift error can be suppressed because the relative moving amount of the handheld medical instrument 21 is used. In addition, the position of the control point viewed from the control reference point is changed in accordance with the moving amount of the handheld medical instrument 21. This can give the operator an intuitive manipulation feeling as if he or she directly manipulated the control point with the distal end of a virtual rod. The steps explained with reference to FIG. 9 will be explained in more detail below.

<S1: Determination of Control Reference Point>

First, the operation of determining the control reference point to be used as a virtual rotation center described in step S1 will be explained. The position/posture measurement device 22 attached to the handheld medical instrument 21 includes a distance sensor for measuring the relative distance between the sheath tube 23 and the distal end of the handheld medical instrument 21, and at least one inertia sensor capable of measuring a 3-axis posture. In this combination of the distance sensor and the inertia sensor, offset between the rotation center of the abdominal wall 5 and the measurement origin of the distance sensor is unknown, and a drift error occurs for a rotation around the gravity axis. However, this drift error is normally negligibly small within a short time of a few seconds to a few minutes, so a drift of the measurement value need not be taken into consideration. That is, manipulation of the end effector performed by using the handheld medical instrument 21 according to this embodiment is completed for about a few minutes in practice, and the mode is switched to an actual surgery using the handheld medical instrument 21. Therefore, drift errors accumulated in this period are negligibly small. Even if this end effector manipulation using the handheld medical instrument 21 requires a long time, it is possible to temporarily switch the manipulation mode to an actual surgery using the handheld medical instrument 21, and then switch the mode to the end effector manipulation again. Consequently, each manipulation can be performed within a time period during which drift errors are negligible.

Calibration is performed in a state in which the robot medical instrument 12 and the handheld medical instrument 21 held by the operator are inserted into the body cavity through the sheath tube 14 and the sheath tube 23, respectively. More specifically, the operator moves the end effector 13 to a position where the distal and of the handheld medical instrument 21 can come in contact with the end effector 13. In this case, the operator manually moves the end effector 13 (by performing a jog operation or the like), and stops the end effector 13 when it arrives at the target position. In this state, the control unit 4 obtains sensor information (current position information) of each joint from the medical instrument driving unit 11, and obtains the posture of the end effector 13 in the coordinate system of the robot by solving well-known forward kinematics. In addition, from the information of the position/posture measurement device 22, the control unit 4 can obtain the relative distance between the sheath tube 23 and the distal end of the handheld medical instrument 21, and the posture of the handheld medical instrument, in the coordinate system of the inertia sensor. This inertia sensor coordinate system rotates for a long time period due to drift errors described above, but can be regarded as not rotating for a unit time of a few seconds or a few minutes.

Figure 2:
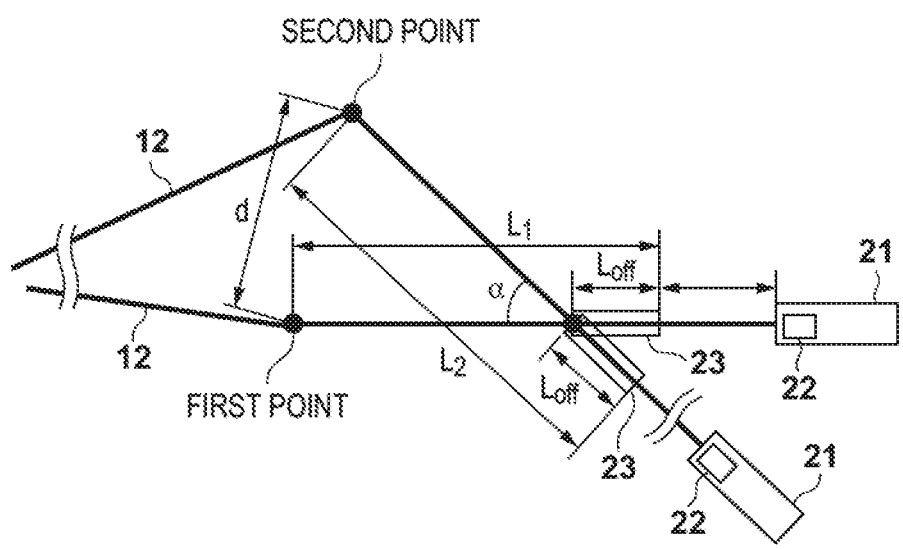
FIG. 2 is a view for explaining a calibration method for obtaining the relationship between the coordinate system of a robot and the coordinate system of an inertia sensor according to the embodiment.

Then, as shown in FIG. 2, the distal end of the handheld medical instrument 21 is brought into contact with at least two points already known in the coordinate system of the robot. The control unit 4 holds measurement values output from the distance sensor and the inertia sensor at the timing of this contact. Note that in order to bring the handheld medical instrument 21 into contact with the two points in the coordinate system of the robot, the operator can cause the display unit 7 to display an image obtained from a laparoscope (not shown) separately inserted into the body cavity, and perform manipulation while watching the displayed image.

In addition, the control unit 4 calculates the forward kinematics of the robot, and calculates the positions of the two contact points in the robot coordinate system. The two contact points are, for example, the positions of the distal and proximal ends of the end effector 13. However, the two positions can be any arbitrary positions as long as they are mechanically already known positions. It is also possible to bring the first point into contact, and then move the robot to a different position and bring the second point into contact. If two or more robot arms exist, points on the individual end effectors can be the contact points. However, if the two contact points exist on the gravity axis, rotation around the gravity axis cannot be obtained, so the two contact points are so set that a straight line connecting the two contact points and the gravity axis make an angle. Desirably, the two contact points are set on a plane perpendicular to the gravity axis (that is, a plane parallel to the ground). For example, the control unit 4 calculates the difference between the positions of the two contact points on the gravity axis, and displays the differential value (for example, −3, . . . , −1, 0, +1, . . . , +3) on the display unit 7. This enables the user who moves the robot to easily adjust the two contact points on the plane perpendicular to the gravity axis.

Furthermore, the control unit 4 convers the value of the distance sensor into the insertion depth based on the rotation center of the abdominal wall. Also, since the two contact points are already known in the robot coordinate system, the control unit 4 can obtain a distance d between the two points as follows:

$$d=|p_2-p_1| \qquad (1)$$

where $p_1$ and $p_2$ are the positions, in the robot coordinate system, of the two contact points between the handheld medical instrument 21 and the end effector 13.

On the other hand, the control unit 4 obtains, from the information of the inertia sensor, a vector when the handheld medical instrument 21 comes in contact with the two points of the end effector 13, and calculates an angle α between the two points by inner product. In addition, the control unit 4 measures the distance based on the sheath tube 23, from the information of the distance sensor. Letting $L_1$ and $L_2$ be the relative distances from the two contact points to the sheath tube 23, and $L_{off}$ be the distance between the reference point of the distance sensor and the rotation center, the two lengths have the following relationship:

$$(L_1-L_{off})^2+(L_2-L_{off})^2-2(L_1-L_{off})(L_2-L_{off})\cos\alpha=d^2 \qquad (2)$$

In the above equation, $L_1$ and $L_2$ need not always represent the distance from the sheath tube 23 to the distal end of the handheld medical instrument 21, and it is also possible to use a distance from another position of the handheld medical instrument 21 by taking account of the sign. Solving the above equation for $L_{off}$ yields only one solution under geometrical conditions, and this solution can be obtained as follows:

$$L_{off} = \frac{-B - \sqrt{B^2 - AC}}{A} \quad (3)$$
$$A = 2(1 - \cos\alpha)$$
$$B = -(L_1 + L_2)(1 - \cos\alpha)$$
$$C = L_1^2 + L_2^2 - d^2 - 2L_1 L_2 \cos\alpha$$

<S2: Conversion from Coordinate System of Inertia Sensor to Coordinate System of Robot>

The step of converting the coordinate system of the inertia sensor to the coordinate system of the robot will be explained in more detail below. The control unit 4 obtains the positions of the two contact points, as $q_1$ and $q_2$, in the inertia sensor coordinate system using the rotation center as the origin. Since these points correspond to the two points $p_1$ and $p_2$ in the robot coordinate system, an evaluation function H below can be formed by using a rotation matrix R and a translation vector t.

$$H = \sum_{i=1}^{N} \|p_i - (Rq_i + t)\|^2 \quad (4)$$

The inertia sensor coordinate system is converted into the robot coordinate system by obtaining the rotation matrix R and the translation vector t that minimize the evaluation function. Note that the rotation matrix R and the translation vector t contain a total of six variables, so six equations can be formed by using a condition including two different contact points. Accordingly, the solution can be converged when the robot and the handheld medical instrument 21 are brought into contact with each other in at least two points. It is, of course, also possible to optimize the evaluation function by using two or more points.

<S4: Calculation of Reference Vector Heading from Control Reference Point to Control Point>

Figure 3:
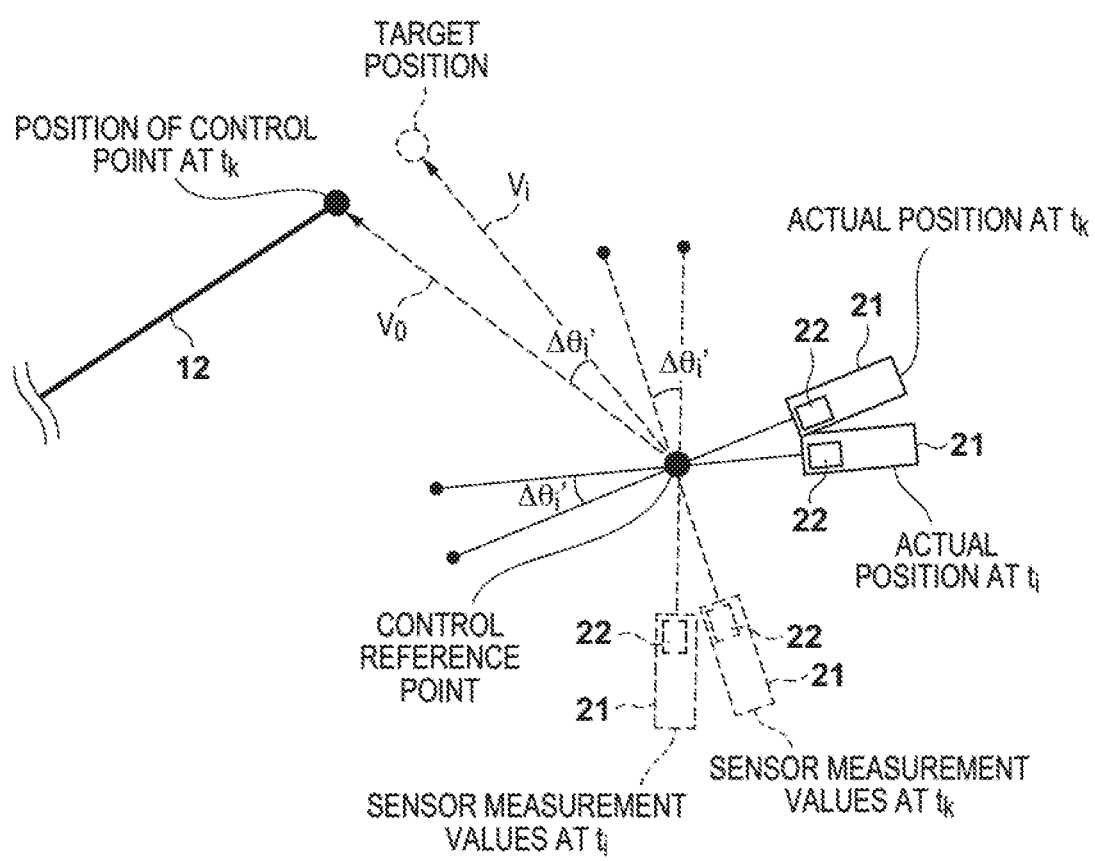
FIG. 3 is a view for explaining a process of determining a target position with respect to a control point of a robot medical instrument according to the embodiment.

The operation of calculating the reference vector heading from the control reference point to the control point will be explained in more detail below with reference to FIG. 3. First, the control unit 4 obtains the control point as an arbitrary point that can be defined in the robot coordinate system. The control point can be the distal end of the robot medical instrument 12, or the proximal end or the distal end of the end effector 13. The control point can also be defined in the space if the robot can be positioned. In this embodiment, an example in which the proximal end of the end effector 13 manipulated by the handheld medical instrument 21 is the control point will be explained. The control unit 4 obtains the position of the control point from the current position information obtained from the medical instrument driving unit 11. Also, the control unit 4 sets the rotation center of the handheld medical instrument 21 as the control reference point.

Let $p_c$ be the position of the control point at a moment at which the operator has switched the manipulation mode to the position control mode. Also, let $p_t$ be the position of the already determined control reference point. Under the conditions, the control unit 4 calculates a vector $v_0$ (that is, a reference vector) heading from the control reference point $p_t$ to the control point $p_c$ of the medical instrument in accordance with the following equation:

$$v_0 = p_c - p_t \quad (5)$$

The control unit 4 performs this calculation only at a moment at which the mode switching unit 3 has switched the manipulation mode to the position control mode, and holds the reference vector $v_0$ as a constant until the position control mode is canceled. The reference vector $v_0$ is represented by polar coordinates as follows:

$$v_0 = \begin{pmatrix} x_0 \\ y_0 \\ z_0 \end{pmatrix} = \begin{pmatrix} l_0 \cos\phi_0 \cos\theta_0 \\ l_0 \cos\phi_0 \sin\theta_0 \\ l_0 \sin\phi_0 \end{pmatrix} \quad (6)$$

<S5: Calculation of Relative Moving Amounts of Handheld Medical Instrument>

Let $(l'_k, \phi'_k, \theta'_k)$ be the sensor measurement values of the handheld medical instrument 21 at a moment $t_k$ at which the operator has switched the manipulation mode to the position control mode by using the mode switching unit 3. Letting $t_i$ be time at which the handheld medical instrument 21 is moved to a given position from the moment described above, individual changed values can be represented by $(l'_{k+i}, \phi'_{k+i}, \theta'_{k+i})$. Then, the control unit 4 calculates the change amounts of the measurement values as follows, as the relative moving amounts of the handheld medical instrument 21 described above:

$$\Delta l'_i = l'_{k+i} - l'_k$$
$$\Delta \phi'_i = \phi'_{k+i} - \phi'_k$$
$$\Delta \theta'_i = \theta'_{k+i} - \theta'_k \quad (7)$$

Note that the relative moving amounts $(\Delta l'_i, \Delta \phi'_i, \Delta \theta'_i)$ are obtained within a short time of a few seconds to a few minutes during which the position control mode is set, so it is unnecessary to take account of a drift error for $\Delta \theta'_i$.

<S6: Determination of Target Position of Control Point>

Furthermore, the control unit 4 calculates a vector $v_i$ from the control reference point to the target position by using the measurement value change amounts (relative moving amounts) of these sensors and the reference vector.

$$v_i = \begin{pmatrix} x_i \\ y_i \\ z_i \end{pmatrix} = \begin{pmatrix} (l_0 + \Delta l'_i)\cos(\phi_0 + \Delta\phi'_i)\cos(\theta_0 + \Delta\theta'_i) \\ (l_0 + \Delta l'_i)\cos(\phi_0 + \Delta\phi'_i)\sin(\theta_0 + \Delta\theta'_i) \\ (l_0 + \Delta l'_i)\sin(\phi_0 + \Delta\phi'_i) \end{pmatrix} \quad (8)$$

Consequently, a vector $p_r$ indicating the target position in the robot coordinate system can be obtained as follows:

$$p_r = p_t + v_i \quad (9)$$

After that, the control unit 4 moves the control point of the end effector 13 to a given target position by using a well-known robot arm control method. No variables represented in this equation are influenced by a drift error. As a consequence, the operator can intuitively manipulate the robot without being aware of the rotation of the coordinate system.

In addition, as described above in the explanation of FIG. 9, the processing of this embodiment enables the operator to intuitively manipulate the control point as if he or she directly manipulated it. In the above-described example, the origin of the handheld medical instrument 21 is the control reference point $p_r$. Therefore, the operator recognizes as if a virtual shaft extending from the rotation center to the control point existed and he or she manipulated the control point by holding the shaft in his or her hand.

In this embodiment as explained above, the target position of the control point of the robot medical instrument 12 or the like is determined based on the relative moving amounts of the handheld medical instrument 21 from the reference time (the start time of the position control mode) at which the manipulation of the robot medical instrument 12 is started. This suppresses the influence of a drift error in the coordinate system of the inertia sensor, and enables the operator to intuitively control the position of a desired point on the robot arm by using the handheld medical instrument. In other words, it is possible to intuitively control the posture of a mechanically controlled surgical tool by using a surgical tool for a medical treatment, while suppressing the influence of a measurement error.

Note that the process of obtaining the control reference point and the process for calibration can be simplified by the configuration of a robot medical instrument to be adopted or a necessary application. For example, assume that one arbitrary axis of the robot coordinate system points in the gravity direction. In a situation like this, conversion between the inertia sensor coordinate system and the robot coordinate system can be performed by obtaining only translation and rotation around the gravity axis, and the calculation can be performed by using an analysis solution. Also, even when one arbitrary axis of the robot coordinate system does not match the gravity axis, the robot coordinate system can be converted into a coordinate system in which at least one axis is parallel to the gravity axis by attaching an acceleration sensor to the robot. That is, the abovementioned simplified calculation may also be performed after the coordinates are converted.

Several methods are available as the method of matching the reference point of the distance sensor with the actual rotation center. For example, in order that the depth of insertion of the sheath tube 23 into the abdominal wall 5 is always constant, it is possible to form a mark in a predetermined position of the sheath tube 23, or attach a stopper to the sheath tube 23 so as to prevent insertion more than the constant depth. When the depth of insertion of the sheath tube 23 into the abdominal wall 5 is constant, the origin of the distance sensor can be offset to the rotation center.

Also, a measurement device capable of measuring the position of an arbitrary point on the robot coordinate system can be used to measure the position of a point of the robot. Examples of a measurement device like this are a mechanical device for measuring the position of the arm distal end, a device for optically measuring the position, and a device for magnetically measuring the distance. These measurement devices can normally be integrated with the robot coordinate system in advance, and hence can measure an arbitrary position on the robot coordinate system. In addition, when the position of the rotation center of the handheld medical instrument 21 is obtained by using a device like this, the obtained coordinate system of the handheld medical instrument 21 can be integrated with the robot coordinate system.

Furthermore, it is also possible to select a predetermined control reference point from control reference points determined beforehand without following the above-described procedures of calibration. In this case, templates defining places where the origin of the handheld medical instrument 21 exists are prepared, and the operator need only select an arrangement closest to a surgery to be performed. When integration to the robot coordinate system is possible, an arbitrary point on a three-dimensional space can be designated. Thus, the control reference point need not always exist in the rotation center of the handheld medical instrument, and any point on the robot coordinate system can be determined by selection or a calculation in accordance with an application.

(Control of Posture of End Effector)

An example of controlling the position of the proximal end of the end effector 13 has been explained above. However, in addition to the control of the position based on the proximal end of the end effector, it is also possible to take account of the posture of a portion existing ahead of the proximal end. For example, control can also be so performed as to fix the posture with respect to a predetermined point in the robot coordinate system so that the distal end always points to a predetermined point. It is also possible to perform control so as to simply move only the position of the control point with the joint being fixed.

An example in which the series of operations described above are applied to the posture control of the end effector 13 will be explained below. To control the posture of the end effector 13, the mode switching unit 3 includes a posture control mode for manipulating the posture, in addition to the position control mode for manipulating the position of the end effector 13.

An example of a combination of the control reference point and the control point which the operator can intuitively manipulate when performing posture control is a combination of the rotation center of the handheld medical instrument 21 and the distal end of the end effector 13. The following explanation will be made by taking this combination as an example. However, the combination can be any arbitrary combination of points that can be defined in the robot coordinate system.

In the posture control mode, to make only the posture of the end effector 13 changeable, another control point (for example, the position of the proximal end) of the end effector (which is used in position control) is fixed to the position. The point to be fixed (a fixed point) need not always be the control point. When the end effector 13 has a plurality of control points, however, it is also possible to sequentially change control targets by setting one of the plurality of control points as a current control target, and set a control point different from the current control target as the fixed point. A point to be set as the fixed point can be changed in accordance with the configuration of the robot or a method of using the robot. For example, assuming that a medical instrument has a bending joint at the distal end of a rod-like shaft, the center of the bending joint is set as the fixed point, and only the posture of a portion existing ahead of the fixed point is controlled.

Figure 4:
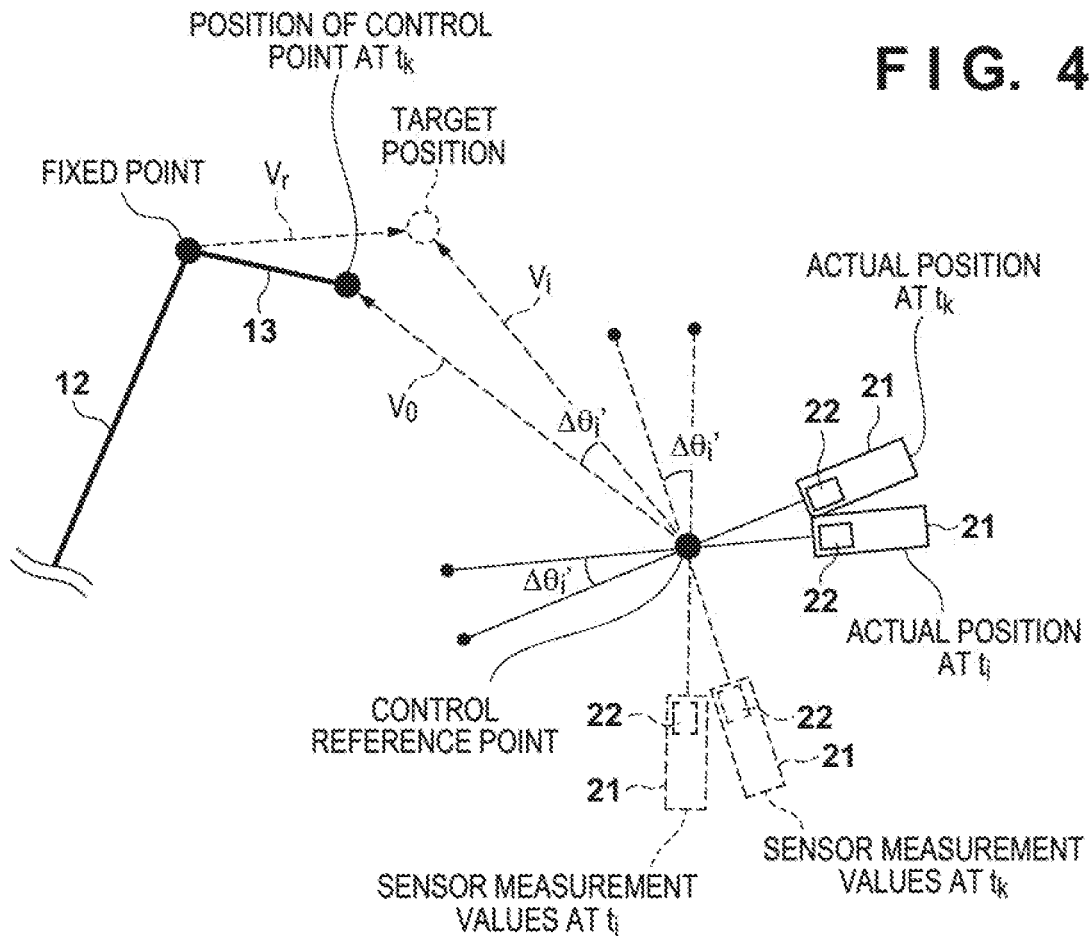
FIG. 4 is a view for explaining the process of determining the target position with respect to the control point of the robot medical instrument according to the embodiment.

Control in the posture control mode will be explained with reference to FIG. 4. The basic control process in the posture control mode is the same as that in the position control mode. First, assuming that steps S1 and S2 described above are already executed, if the control unit 4 receives a notification for switching to the posture control mode instead of step S3, the process advances to step S4, and the control unit 4 calculates the reference vector $v_0$ heading from the rotation center (control reference point) to the control point at the moment at which the modes are switched. Then, in step S5, the control unit 4 obtains the relative moving amount of the handheld medical instrument 21 by using information obtained from the inertia sensor or the like. In step S5, the control unit 4 determines the target position $p_r$ of the robot.

In the posture control mode, the proximal end or the like of the end effector is fixed by the fixed point, control for moving the control point to the target position is sometimes physically restricted. Therefore, a vector heading from a fixed point $p_f$ to the target position $p_r$ is calculated and input as a target posture $v_r$ to the robot. This $v_r$ represents a target posture on the robot coordinate system. Since the robot can freely control the posture of the end effector, the operator can intuitively control the posture of the end effector by using the handheld medical instrument 21 while suppressing the influence of a drift error.

(Application Examples of Posture Control of Robot Medical Instrument)

Posture control of the robot medical instrument 12, that is, control using the control point, the fixed point, and the rotation center (control reference point) of the handheld medical instrument 21 is applicable to various manipulations.

Figure 5:
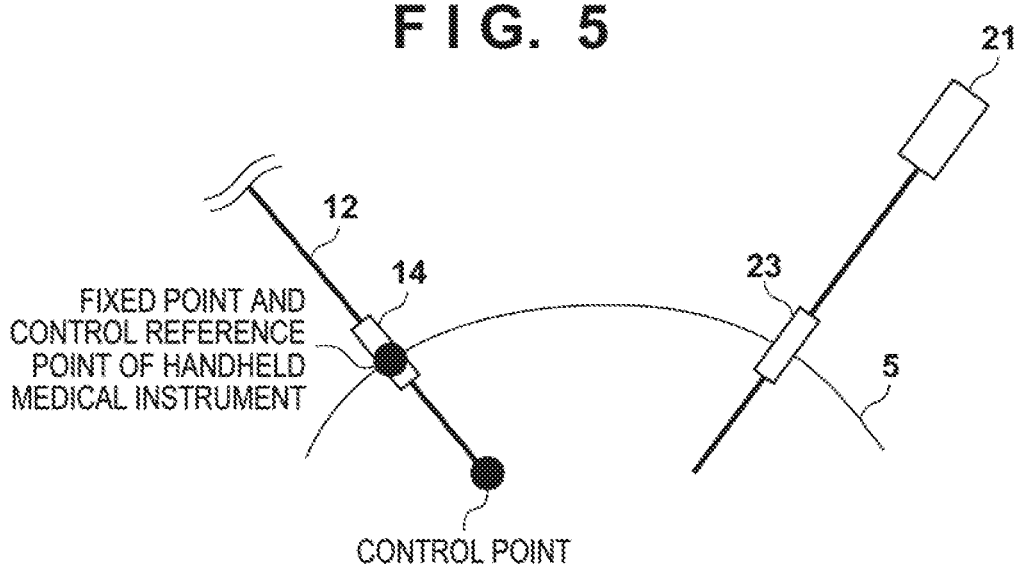
FIG. 5 is a view for explaining control of a rod-like robot medical instrument according to the embodiment.

For example, as shown in FIG. 5, assume that a case in which the robot medical instrument 12 is a rod-like medical instrument and the robot can freely change the posture will be explained. Since this medical instrument is inserted into the body cavity through the sheath tube 14, the rotation center in the abdominal wall 5 exists on the robot side as well. The above-described fixed point is set in the position of the rotation center on the robot side, the control reference point of the handheld medical instrument 21 is virtually moved to the fixed point, and the distal end of the rod-like medical instrument is selected as the control point. Consequently, the operator can manipulate the medical instrument on the robot side as if he or she held the medical instrument in his or her hand. Note that in this case, the fixed point functions as the rotation center, and the degree of freedom in a linear-motion direction is permitted.

Figure 6:
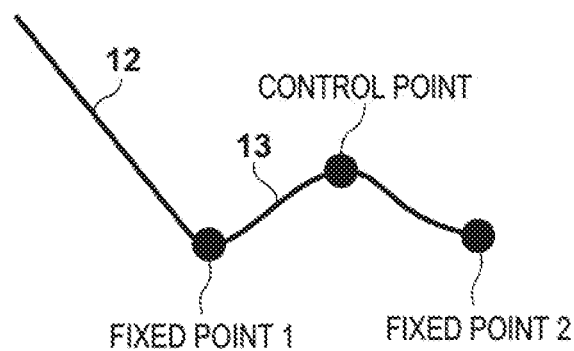
FIG. 6 is a view for explaining control of the posture of a robot medical instrument having a plurality of degrees of freedom according to the embodiment.

Another example is the robot medical instrument 12 having a plurality of degrees of freedom shown in FIG. 6. Assume that this medical instrument can be changed to an arbitrary shape by an actuator, and an arbitrary point of the medical instrument can be controlled in the robot coordinate system. In this case, the fixed points are set in the distal end and another point apart from the distal end, and a point between these fixed points is selected as the control point. The control reference point can be the position of the actual rotation center of the handheld medical instrument 21. In this example, the posture of a part of the medical instrument can be changed while fixing a point that is unmovable due to an obstacle or the like. If the control point is physically unable to follow the input value, only the posture vector can be changed by applying the example of the posture control mode described above. It is also possible to give the robot medical instrument 12 a plurality of control points, select one of the plurality of control points as a target of posture control, and set other control points as the fixed points. In this case, posture control is performed on the control point as a control target while sequentially switching the control point and the fixed point by toggle manipulation or the like. In this example shown in FIG. 6, the control point and fixed point 2 are switched. When sequentially switching the control points, the start time of the posture control mode can also be reset. This can reduce the influence of a drift error.

Figure 7:
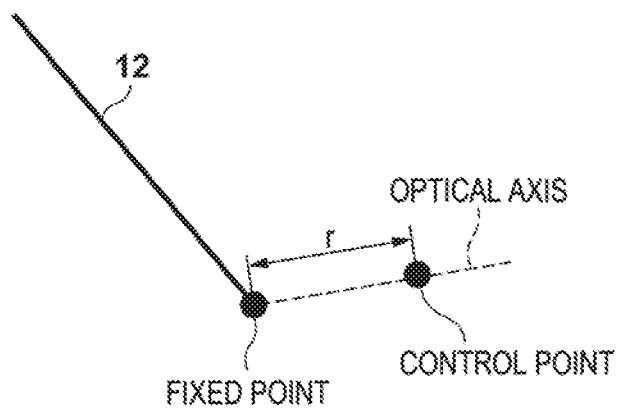
FIG. 7 is a view for explaining control of the posture of a robot medical instrument capable of changing the direction of the optical axis according to the embodiment.

The above-described control point, fixed point, and control reference point need not be physically actually existing points, and can move to virtual positions in accordance with a purpose. Also, as each of these points, two or more points can exist. The control point may also be, for example, a point on the optical axis. For example, as shown in FIG. 7, assume that a medical instrument capable of changing the direction of the optical axis is the robot medical instrument 12. In this case, the starting point of bending of the optical axis is set as the fixed point, and a point on the optical axis, which exists apart from the fixed point by a distance r, is selected as the control point. A configuration like this makes it possible to control the direction of the optical axis of an optical device attached to the robot medical instrument 12, in the same manner as the control for the end effector.

(Manipulation of Robot Medical Instrument Combined with Another Manipulating Member)

Figure 8:
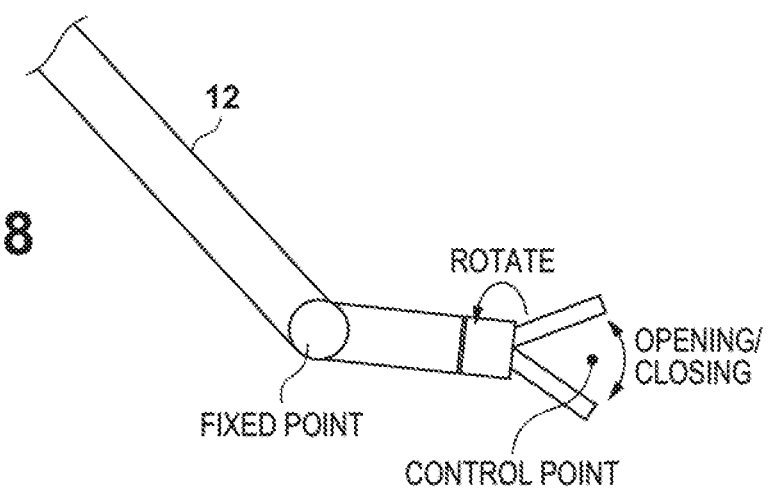
FIG. 8 is a view for explaining control of the posture of a robot medical instrument including another mechanism according to the embodiment.

It is possible to intuitively manipulate an end effector having a form including a joint or the like by further combining another manipulating member. For example, assume that the robot medical instrument 12 is a forceps-like medical instrument having a jaw mechanism that rotates and opens/closes at the distal end as shown in FIG. 8. When manipulating this medical instrument having the jaw mechanism, an input device dedicated to opening/closing of the jaw is installed. For example, a switch, a dial, or the like for opening/closing the jaw mechanism can be attached to the handheld medical instrument 21. Instead, it is also possible to manipulate the opening/closing by a foot switch or a voice.

A dedicated input device such as a switch or a dial can be used for the rotation of the distal end as well, but the rotation of the distal end can also be controlled from the posture information of the handheld medical instrument. At the timing at which the operator has switched the manipulation mode to the robot manipulation mode (regardless of whether the mode is position control or posture control), the control unit 4 sets the rotational angle around the shaft of the handheld medical instrument 21 and the rotational angle of the distal end of the end effector 13 to 0°. Then, the control unit 4 measures, by using the inertia sensor, the relative angle when the handheld medical instrument 21 is rotated around the shaft from this state, and inputs the measurement value as the rotational angle of the distal end of the end effector 13. This makes it possible to control the rotation of the distal end of the end effector, in addition to the control method described above. Note that control like this makes the rotational angle unaffected by a drift error.

In the above-described embodiment, the case in which the position control mode and the posture control mode are separately controlled has been explained. However, it is also possible to execute these control modes in parallel. For example, one of the position control mode and the posture control mode may also be manipulated by input different from the insertion angle and the insertion depth of the handheld medical instrument 21. For example, the position control mode is controlled by the insertion angle and the insertion depth of the handheld medical instrument 21 described above, and at the same time the posture of the end effector 13 is changed by a manipulating member such as a switch attached to the handheld medical instrument. In this case, position control of the end effector is manipulated by the posture of the handheld medical instrument 21, and posture control of the end effector is performed from the hand switch. This is advantageous in that the position control and posture control of the end effector can be performed at the same time. Note that it is also possible to switch the manipulation targets and perform the position control of the end effector from the hand switch or the like.

(Application for Setting Parameters of Robot Arm)

The above-described control can be used not only to manipulate the robot medical instrument 12, but also as an input device for changing various parameters of the medical instrument driving unit 11 (a robot arm). In this case, the mode switching unit 3 can further set a parameter changing mode, and the control unit 4 obtains parameters from the medical instrument driving unit 11 or the nonvolatile memory 8, and displays a parameter to be set on the display unit 7. When the mode switching unit 3 sets the parameter changing mode, the medical instrument driving unit 11 is fixed to the posture at that time, and control parameters set in the medical instrument driving unit 11 are made changeable. The changeable parameters include all parameters pertaining to manipulation, such as the magnification of a motion amount (motion scaling) with respect to an input amount, the velocity, the power, and the limitation on a movable range. An example of a case in which the gripping force is changed will be explained. When the parameter changing mode is set, the posture of the handheld medical instrument 21 can be handled as an input device such as a general volume controller. For example, the control unit 4 increases the gripping force when the handheld medical instrument 21 is rotated clockwise around the shaft, and decreases the gripping force when the rotation is counterclockwise. Since the control unit 4 displays the way the parameter as a manipulation target is changed on the display unit 7, the operator (or the manipulator) can grasp the current value. The display method can be any of, for example, a numerical value, a graph, a sound volume, a musical interval, a vibration strength, the brightness of light, and a color. A parameter can also be changed by using a physical amount that can be calculated from posture information. Examples are the insertion amount, the inclination, the moving velocity, the rotational speed, an input that gives impact, an input that gives vibration, and a specific figure drawn by the distal end of the handheld medical instrument 21. That is, various input methods are possible.

(Intuitive Manipulation of Robot Medical Instrument Capable of Imaging)

An example of a medical instrument assumed as a robot medical instrument is a device, such as an endoscope, which is obtained by attaching an optical part (for example, a lens or an optical fiber) to the vicinity of the distal end of the shaft of the medical instrument, images object light entering from the optical part, and outputs an image signal. Medical instruments like this are not only a medical instrument in which the central axis of the shaft of the medical instrument matches the optical axis of the optical part. That is, in many medical instruments such as a forward-oblique viewing endoscope and an endoscope having a distal end that bends, the direction of the shaft of the robot medical instrument 12 and the direction of the optical axis are different. Note that an optical part in the following explanation is an optical part installed in a position where light entering from outside the lens barrel of the robot medical instrument 12 enters the lens barrel (that is, a part on the object side).

A case in which the operator manipulates an endoscope like this as if he or she held the robot medical instrument 12 in his or her hand by control using the fixed point and the control point explained with reference to FIG. 5 will be explained below. That is, the rotation center of the robot medical instrument 12 in the abdominal wall 5 is set at the fixed point, the control reference point of the handheld medical instrument 21 is virtually set in the position of the fixed point, and the control point (an optical part attaching position) at the distal end of the shaft of the robot medical instrument 12 is controlled. In this state, the optical part attached to the shaft distal end of the robot medical instrument 12 is fixed such that the optical axis makes a predetermined angle to the central axis of the shaft.

Figure 10:
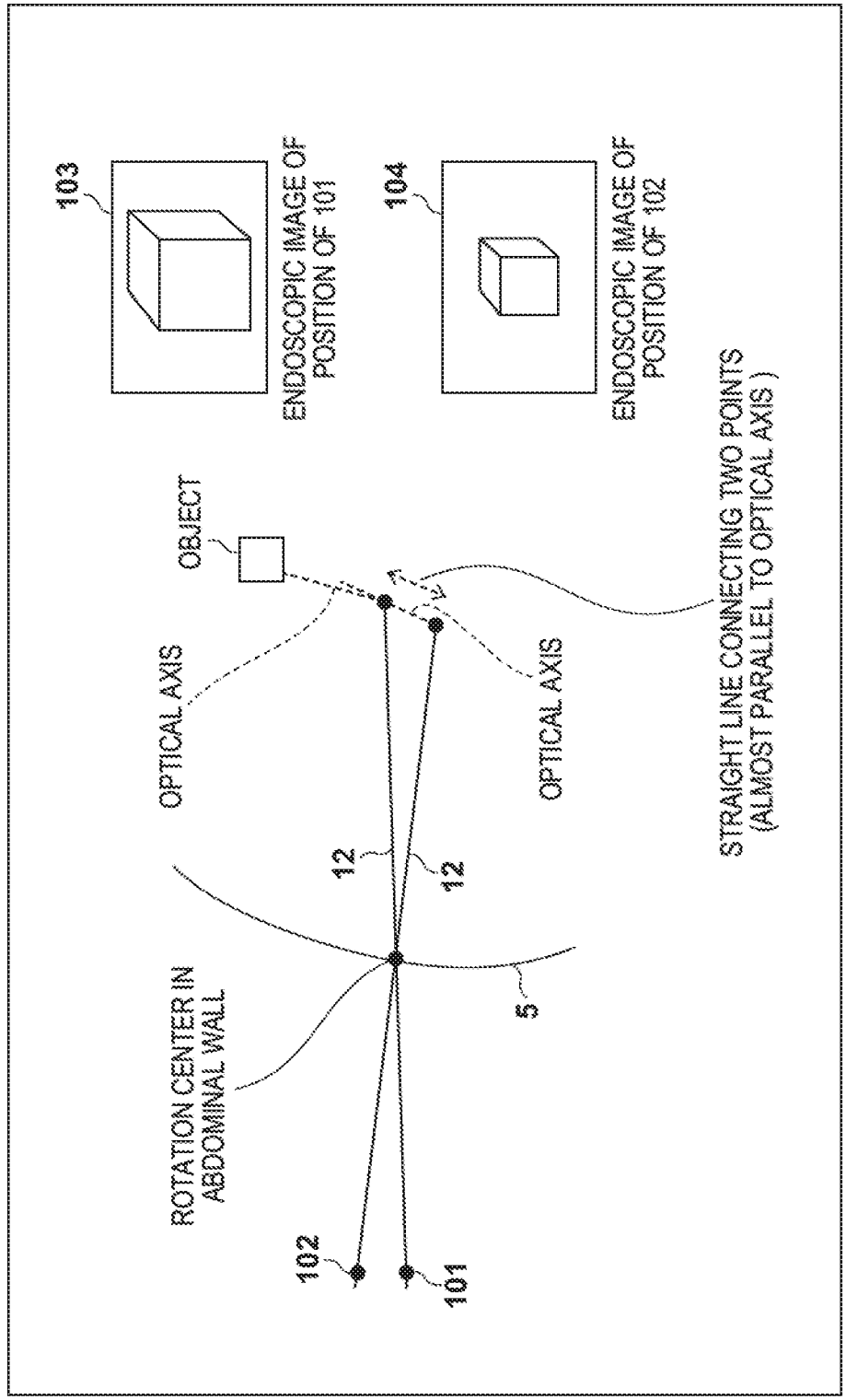
FIG. 10 is a view for explaining manipulation of a robot medical instrument including an imaging device.

A state in which the operator manipulates the robot medical instrument 12 will be explained with reference to FIG. 10. FIG. 10 shows the way an object inside the abdominal wall is imaged by using an optical part having an optical axis inclined to the central axis of the shaft of the robot medical instrument 12. In FIG. 10, the optical axis of the optical part points to the object, and the object does not exist in the direction of the central axis of the shaft of the robot medical instrument 12. When, for example, the operator manipulates the handheld medical instrument 21 and moves a virtual grip position 101 on the robot medical instrument 12 to a position 102 (by sliding) in this state, an endoscopic image captured via the optical part changes from an endoscopic image 103 to an endoscopic image 104 like zooming out. This produces a large difference between the direction of manipulation by the operator and the endoscopic image changing direction. If this difference is very large, the operator sometimes feels unnaturalness in manipulation.

Accordingly, in order to reduce the difference between the direction of manipulation performed on the handheld surgical tool by the operator and the image changing direction, the operator is allowed to control the robot medical instrument 12 as if he or she manipulated the direction of the optical axis by holding a virtual rod sharing the optical axis. That is, when the operator manipulates the handheld medical instrument 21 by sliding it with respect to the rotation center of the abdominal wall as a base point, the robot medical instrument 12 is so controlled as to pan the endoscopic image in the manipulation direction.

More specifically, a camera coordinate system defining the posture of the optical part and the robot coordinate system are integrated by calibration, and the direction of the virtual rod that passes the position of the optical part (that is, the control point) and is almost the same as the direction of the optical axis of the optical part is determined. Then, the fixed point is set on the axis of the determined virtual rod, and the position of the control point is controlled in accordance with operator's manipulation by using the fixed point as a base point. Note that the fixed point set on the axis of the virtual rod is also the control reference point.

Calibration first causes the display unit 7 to display an endoscopic image containing an object to be imaged. In this case, the posture of the robot medical instrument 12 is determined such that a specific position of the object (for example, the center of the object) comes to the center of the screen. In this state, the control unit 4 records the position of the optical part (the position of the distal end of the endoscope) in the robot coordinate system. Then, the posture of the robot medical instrument 12 is manually changed so that the size of the object to be imaged changes (that is, the object is zoomed in or out), and the position of the optical part in this state is recorded. In this case, the abovementioned specific position of the object is set in almost the center of the screen. "The specific position is set in almost the center of the screen" because the direction of the optical axis is fixed to the central axis of the shaft of the robot medical instrument 12, so the specific position of the object is not strictly the center of the screen in some cases. If the distance between two recorded positions is short, however, a straight line passing the two recorded positions can be approximated to be almost the same as the direction of the optical axis of the optical part, as indicated by the distal end position of the robot medical instrument 12 shown in FIG. 10. Accordingly, this straight line can be determined as a virtual rod sharing the optical axis. Generally, the posture around the optical axis is determined because the horizontal direction of the screen is parallel to the ground. Also, since the origin of the camera coordinate system almost matches the distal end of the endoscope, the position and posture of the camera coordinate system viewed from the robot coordinate system are obtained.

Note that calibration performed by using an endoscopic image is necessary when using the robot medical instrument 12 having the robot coordinate system not integrated with the camera coordinate system. However, the coordinate systems can also be integrated by another method if a transformation matrix or the like between the coordinate systems is obtained in advance. Also, when using an endoscope having a degree of freedom by which the distal end bends, the correspondence between the camera coordinate system and the robot coordinate system changes if bending of the distal end changes. Even in a case like this, this method is applicable when the abovementioned calibration is performed whenever the bending angle is changed. It is also possible to integrate the camera coordinate system and the robot coordinate system by using a sensor capable of obtaining the bending angle of the distal end.

Figure 11:
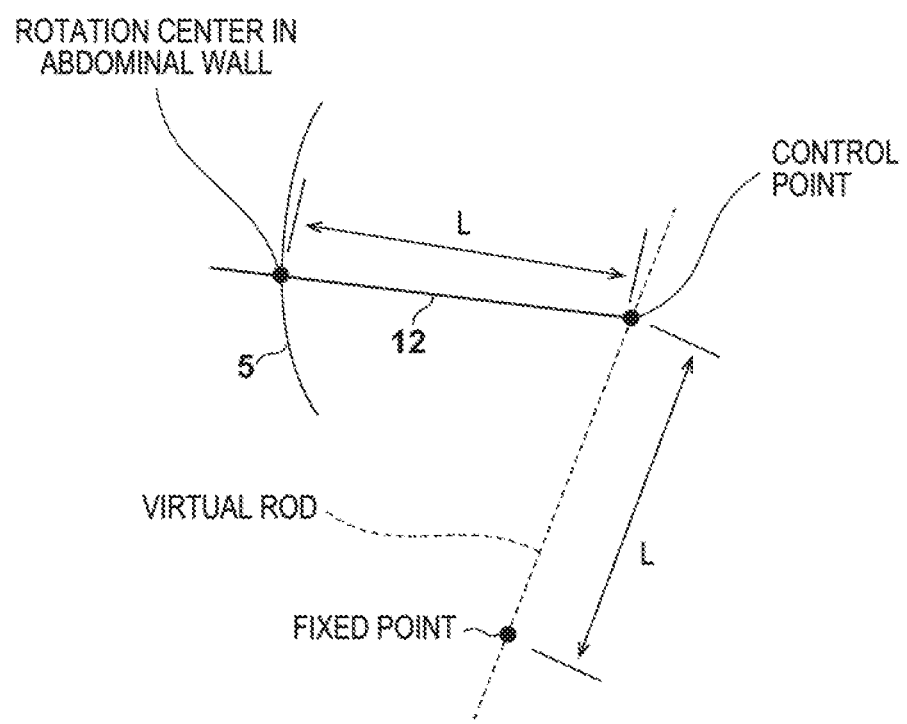
FIG. 11 is a view for explaining control of the robot medical instrument including the imaging device according to the embodiment.

Then, the control point is set in the position of the optical part (the origin of the camera coordinate system) in order to control the obtained position and posture of the camera coordinate system. This position is, for example, the distal end position of the endoscope as described above. As shown in FIG. 11, the fixed point is set on a virtual rod and in a position offset by a distance (L) between the origin of the camera coordinate system and the rotation center of the endoscope in the abdominal wall. In addition, the position of the control reference point of the handheld medical instrument is set in the obtained position of the fixed point. By thus setting the control point and the fixed point, an operator can perform intuitive manipulation as if he or she directly held and moved a virtual rod in the same direction as the optical axis of the optical part, regardless of the direction of the optical axis of the optical part with respect to the shaft of the surgical tool. Note that the control point and the fixed point can basically be set when the manipulation mode is switched to the position control mode or the posture control mode. Note also that the robot medical instrument 12 includes only an optical part at the distal end of the shaft in the example explained above, but the optical part may also be integrated with an imaging element. Furthermore, the positions of the control point and the fixed point need not always be the above-described positions, and it is also possible to change the amplitude of the virtual rod by increasing or decreasing the distance between the two points.

Note that in the above-described embodiment, an example in which the operator intuitively manipulates the posture of the end effector by using the position/posture measurement device 22 that causes a drift error has been explained. However, this manipulation can also be implemented by using the position/posture measurement device 22 capable of obtaining an absolute position.

Note also that the above-described embodiment can also be implemented by a processor in a computer of the above-described system or apparatus by reading out a program obtained from a network and executing the program.

The present invention is not limited to the above embodiment, and various changes and modifications can be made without departing from the spirit and scope of the invention. Therefore, to apprise the public of the scope of the present invention, the following claims are appended.

What is claimed is:

1. A surgery assisting apparatus, comprising:
   a controller configured to control a posture of a first surgical tool that is inserted into a body cavity and that is driven mechanically;
   a measurement device that includes at least one sensor and is configured to measure an amount of change in a posture of a second surgical tool that is inserted into the body cavity and that is operated directly by an operator; and
   a switch configured to switch between a first mode in which the second surgical tool is used as a treatment tool to perform a medical treatment and a second mode in which the second surgical tool is used as a guide tool to guide the posture of the first surgical tool controlled by the controller, wherein
   the controller controls the posture of at least part of the first surgical tool according to the amount of change measured by the measurement device when the switch is switched to the second mode.

2. The surgery assisting apparatus according to claim 1, wherein the switch includes a hand switch or a foot switch.

3. The surgery assisting apparatus according to claim 2, wherein the at least one sensor of the measurement device includes an inertia sensor mounted to the second surgical tool.

4. The surgery assisting apparatus according to claim 3, wherein the second mode of the switch includes:
   a position control mode of controlling the posture of an entirety of the first surgical tool by the second surgical tool; and
   a posture control mode of controlling the posture of a part of the first surgical tool by the second surgical tool, wherein
   when the switch is switched to the position control mode, the controller moves a control point that is part of the first surgical tool toward a target position that is set according to the amount of change measured by the measurement device, so as to control the posture of the entirety of the first surgical tool, and
   when the switch is switched to the posture control mode, the controller moves the control point, which is provided on a distal end side of a fixed point that is part of the first surgical tool, toward a target position that is set according to the amount of change measured by the measurement device, while keeping a position of the fixed point unchanged, so as to control the posture of the part of the first surgical tool.

5. The surgery assisting apparatus according to claim 4, wherein the switch is configured to further switch to a third mode in which calibration is performed, in addition to the first mode and the second mode, wherein
   when the switch is switched to the third mode, the controller specifies a relationship between a first coordinate system that defines the posture of the first surgical tool driven mechanically and a second coordinate system that defines the posture of the second surgical tool measured by the measurement device, and
   when the switch is switched to the second mode, the controller sets the target position of the control point of the first surgical tool according to the amount of change measured by the measurement device, based on the relationship between the first coordinate system and the second coordinate system specified in the third mode.

6. The surgery assisting apparatus according to claim 5, wherein the controller specifies a direction and a distance from a control reference point set at a predetermined position to the control point, and sets the target position of the control point by changing the direction and the distance from the control reference point by the amount of change measured by the measurement device since a time point when the switch is switched to the second mode.

7. A surgery assisting apparatus, comprising:
a controller configured to control a posture of a first surgical tool that is inserted into a body cavity and that is driven mechanically; and
a measurement device that includes at least one sensor and is configured to measure an amount of change in a posture of a second surgical tool that is inserted into the body cavity and that is operated directly by an operator, wherein
the first surgical tool comprises a joint portion and a movable portion that is located on a distal end side of the joint portion and that is movable in one or a plurality of degrees of freedom, and
the controller performs a first control of controlling a posture of the movable portion according to the amount of change measured by the measurement device, while keeping a position of the joint portion unchanged.

8. The surgery assisting apparatus according to claim 7, wherein the controller performs a second control of controlling the position of the joint portion according to the amount of change measured by the measurement device.

9. A surgery assisting system, comprising:
the surgery assisting apparatus according to of claim 1; and
a medical instrument driving apparatus configured to drive the first surgical tool, in response to an instruction from the controller of the surgery assisting apparatus.

10. A method of controlling a first surgical tool, which is inserted into a body cavity and is driven mechanically, with a surgery assisting apparatus, the method comprising:
measuring a position of and an amount of change in a posture of a second surgical tool that is inserted into the body cavity and that is operated directly by an operator;
switching between a first mode of the surgery assisting apparatus in which the second surgical tool is used as a treatment tool to perform a medical treatment and a second mode of the surgery assisting apparatus in which the second surgical tool is used as a guide tool to guide the posture of the first surgical tool; and
in the second mode, controlling, by at least one processor, a posture of at least part of the first surgical tool according to the measured amount of change in the posture of the second surgical tool.

11. A method of controlling a first surgical tool with a surgery assisting apparatus, wherein the first surgical tool (i) is inserted into a body cavity, (ii) is driven mechanically, and (iii) includes a movable portion and a joint portion, where the movable portion is located on a distal end side of the joint portion and is movable in one or a plurality degrees of freedom, the method comprising:
measuring a position of and an amount of change in a posture of a second surgical tool that is inserted into the body cavity and that is operated directly by an operator; and
controlling, by at least one processor, a posture of the movable portion of the first surgical tool according to the measured amount of change in the posture of the second surgical tool, while keeping a position of the joint portion of the first surgical tool unchanged.

12. A non-transitory computer-readable storage medium that stores a program that causes a surgery assisting apparatus to perform a method of controlling a first surgical tool that is inserted into a body cavity and is driven mechanically, the method comprising:
measuring a position of and an amount of change in a posture of a second surgical tool that is inserted into the body cavity and that is operated directly by an operator;
switching between a first mode of the surgery assisting apparatus in which the second surgical tool is used as a treatment tool to perform a medical treatment and a second mode of the surgery assisting apparatus in which the second surgical tool is used as a guide tool to guide the posture of the first surgical tool; and
in the second mode, controlling a posture of at least part of the first surgical tool according to the measured amount of change in the posture of the second surgical tool.

13. A non-transitory computer-readable storage medium that stores a program that causes a surgery assisting apparatus to perform a method of controlling a first surgical tool, wherein the first surgical tool (i) is inserted into a body cavity, (ii) is driven mechanically, and (iii) includes a movable portion and a joint portion, where the movable portion is located on a distal end side of the joint portion and is movable in one or a plurality degrees of freedom, the method of comprising:
measuring a position of and an amount of change in a posture of a second surgical tool that is inserted into the body cavity and that is operated directly by an operator; and
controlling a posture of the movable portion of the first surgical tool according to the measured amount of change in the posture of the second surgical tool, while keeping a position of the joint portion of the first surgical tool unchanged.

14. The surgery assisting apparatus of claim 1, wherein measuring the amount of change in the posture of the second surgical tool by the measurement device includes measuring an angle and depth of insertion of a shaft of the second surgical tool into the body cavity.

15. The surgery assisting apparatus of claim 7, wherein measuring the amount of change in the posture of the second surgical tool by the measurement device includes measuring an angle and depth of insertion of a shaft of the second surgical tool into the body cavity.

16. The method of claim 10, wherein the measuring of the position of and the amount of change in the posture of the second surgical tool includes measuring an angle and depth of insertion of a shaft of the second surgical tool into the body cavity.

17. The method of claim 11, wherein the measuring of the position of and the amount of change in the posture of the second surgical tool includes measuring an angle and depth of insertion of a shaft of the second surgical tool into the body cavity.

18. The non-transitory computer-readable storage medium of claim 12, wherein the measuring of the position of and the amount of change in the posture of the second surgical tool includes measuring an angle and depth of insertion of a shaft of the second surgical tool into the body cavity.

19. The non-transitory computer-readable storage medium of claim 13, wherein the measuring of the position of and the amount of change in the posture of the second surgical tool includes measuring an angle and depth of insertion of a shaft of the second surgical tool into the body cavity.

* * * * *